(12) United States Patent
Cho et al.

(10) Patent No.: US 12,221,483 B1
(45) Date of Patent: Feb. 11, 2025

(54) FUSION PROTEIN AND NUCLEIC ACID ENCODING SEQUENCE THEREOF, AND USES OF THE SAME

(71) Applicant: China Medical University Hospital, Taichung (TW)

(72) Inventors: Der-Yang Cho, Taichung (TW); Shao-Chih Chiu, Taichung (TW); Shi-Wei Huang, Taichung (TW); Chih-Ming Pan, Taichung (TW); Mei-Chih Chen, Taichung (TW); Yu-Chuan Lin, Taichung (TW); Yeh Chen, Taichung (TW); Yi-Wen Chen, Taichung (TW); Ming-You Shie, Taichung (TW); Kai-Wen Kan, Taichung (TW)

(73) Assignee: CHINA MEDICAL UNIVERSITY HOSPITAL, Taichung (TW)

( * ) Notice: Subject to any disclaimer, the term of this patent is extended or adjusted under 35 U.S.C. 154(b) by 0 days.

(21) Appl. No.: 18/426,912

(22) Filed: Jan. 30, 2024

(51) Int. Cl.
| | |
|---|---|
| *C07K 16/28* | (2006.01) |
| *A61K 38/00* | (2006.01) |
| *A61K 39/00* | (2006.01) |
| *A61P 35/00* | (2006.01) |
| *C07K 14/705* | (2006.01) |

(52) U.S. Cl.
CPC .......... *C07K 16/2809* (2013.01); *A61P 35/00* (2018.01); *C07K 14/70596* (2013.01); *A61K 38/00* (2013.01); *A61K 2039/505* (2013.01); *C07K 2317/569* (2013.01); *C07K 2319/01* (2013.01); *C07K 2319/03* (2013.01); *C07K 2319/30* (2013.01)

(58) Field of Classification Search
None
See application file for complete search history.

(56) References Cited

U.S. PATENT DOCUMENTS

| | | | | |
|---|---|---|---|---|
| 10,617,768 | B2 * | 4/2020 | Lu | A61K 47/65 |
| 11,795,224 | B2 * | 10/2023 | Cho | G01N 33/6872 |
| 2016/0175358 | A1 * | 6/2016 | Jakobovits | A61P 35/02 |
| | | | | 435/372.3 |
| 2022/0306742 | A1 * | 9/2022 | Cho | C07K 16/2809 |

FOREIGN PATENT DOCUMENTS

| | | | | |
|---|---|---|---|---|
| WO | WO-2019175428 A1 * | 9/2019 | | A61K 39/395 |
| WO | WO-2021003445 A1 * | 1/2021 | | C07K 14/70503 |
| WO | WO-2021102585 A1 * | 6/2021 | | A61K 35/761 |
| WO | WO-2021184022 A1 * | 9/2021 | | A61K 9/0019 |
| WO | WO-2021211460 A1 * | 10/2021 | | A61K 9/0019 |

OTHER PUBLICATIONS

Cheng et al. J Am Chem Soc. 2018. 140: 16413-16417 (Year: 2018).*
Liang et al. Theranostics. 2021. 11(7): 3183-3195 (Year: 2021).*
Lin et al. J Drug Targeting. 2019. 28(2): 129-141 (Year: 2019).*
Luo et al. Int J Biol Sci. 2021. 17(10):2476-2486 (Year: 2021).*
Mohammadi et al. BioDrugs. 2023. 37:353-375 (Year: 2023).*
Scott et al. Mol Ther Methods Clin Devel. 2022. 24:355-366 (Year: 2022).*

* cited by examiner

*Primary Examiner* — Zachary S Skelding
*Assistant Examiner* — Brianna K Swartwout
(74) *Attorney, Agent, or Firm* — WPAT, PC

(57) ABSTRACT

The present disclosure provides a fusion protein and the nucleic acid encoding sequence thereof, and uses of the same. The fusion protein of the present disclosure achieves the effect of treating cancer, immunoregulation and activating immune cells through various efficacy experiments.

11 Claims, 18 Drawing Sheets
Specification includes a Sequence Listing.

FUSION PROTEIN AND NUCLEIC ACID ENCODING SEQUENCE THEREOF, AND USES OF THE SAME

STATEMENT REGARDING SEQUENCE LISTING

The sequence listing associated with this application is provided in text format in lieu of a paper copy and is hereby incorporated by reference into the specification. The name of the XML file containing the sequence listing is 112F0614-IE_Sequence_listing. The XML file is 9000 bytes; was created on Jan. 16, 2024.

BACKGROUND OF THE INVENTION

1. Field of the Invention

The present invention relates to a fusion protein and the nucleic acid encoding sequence thereof, and uses of the same.

2. The Prior Art

Cancer, also known as malignancy, is a state of abnormal proliferation of cells, and these proliferating cells may invade other parts of the body as a disease caused by a malfunction in the control of cell division and proliferation. The number of people suffering from cancer worldwide has a growing trend. Cancer is one of the top ten causes of death for the Chinese people and has been the top ten causes of death for consecutive years.

Conventional cancer treatments include surgery, radiation therapy, chemotherapy, and target therapy. Cancer immunotherapy is another method for treating cancer except the above methods. The immune system of the patient is activated in the cancer immunotherapy by using tumor cells or tumor antigens to induce specific cellular and humoral immune responses for enhancing the anti-cancer ability of the patient, preventing the growth, spread, and recurrence of tumors, and achieving the purpose of removing or controlling tumors. However, the current tumor treatments still have the problems of ineffectiveness and strong side effects, and even lead to other immune-related disorders.

CD3ε (CD3 epsilon), a transmembrane protein found on T cells, has been found to be associated with tumors and regulation of immune function. Therefore, researchers have been committed to developing CD3ε as target molecules for tumor identification and regulation of immune function and to find out whether these target molecules have the potential to become anticancer drugs or immunoregulatory drugs. In addition, CD63 is a protein antigen encoded by the CD63 gene in humans. CD63 mainly appears on the surface of extracellular vesicles and also on the surface of ordinary cell membranes. Its encoding gene is related to tumor development.

In order to solve the above-mentioned problems, those skilled in the art urgently need to develop a novel and effective medicament for treating cancer, immunoregulation and activating immune cells for the benefit of a large group of people in need thereof.

SUMMARY OF THE INVENTION

A primary objective of the present invention is to provide a fusion protein, comprising an anti-CD3 single domain antibody and an exosomal protein, wherein the anti-CD3 single domain antibody comprises an amino acid sequence of SEQ ID NO:1, SEQ ID NO:2, and SEQ ID NO:3.

According to an embodiment of the present invention, the anti-CD3 single domain antibody specifically binds to a CD3 ε.

According to an embodiment of the present invention, the exosomal protein is CD63.

According to an embodiment of the present invention, the amino acid sequence of the fusion protein is SEQ ID NO:4.

According to an embodiment of the present invention, the amino acid sequence of SEQ ID NO: 1 is complementarity determining region 1 (CDR1), the amino acid sequence of SEQ ID NO:2 is CDR2, and the amino acid sequence of SEQ ID NO:3 is CDR3.

According to an embodiment of the present invention, the anti-CD3 single domain antibody is an anti-T cell single domain antibody.

Another objective of the present invention is to provide an isolated nucleic acid, encoding the amino acid sequence of the above mentioned fusion protein.

According to an embodiment of the present invention, the isolated nucleic acid consists of nucleotide sequence of SEQ ID NO:5.

Another objective of the present invention is to provide a pharmaceutical composition, comprising the above mentioned fusion protein and a pharmaceutically acceptable carrier.

Another objective of the present invention is to provide a method for treating cancer, immunoregulation and activating immune cells, comprising administering to a subject in need thereof the above mentioned pharmaceutical composition.

According to an embodiment of the present invention, the cancer is treated by penetrating the fusion protein into solid tumors and secreting bispecific T-cell engager (BiTE), and activating peripheral immune cells.

In summary, the fusion protein of the present invention has the effects on treating cancer, immunoregulation and activating immune cells by surface plasmon resonance (SPR), analysis of cytotoxic killing ability, animal experiment, electroporation experiment, testing for transfection efficiency, flow cytometry analysis, in vivo chimeric antigen receptor T-cell therapy (CAR-T), and penetrating the fusion protein into solid tumors and secreting bispecific T-cell engager (BiTE), and activating peripheral immune cells.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

Figure 1:
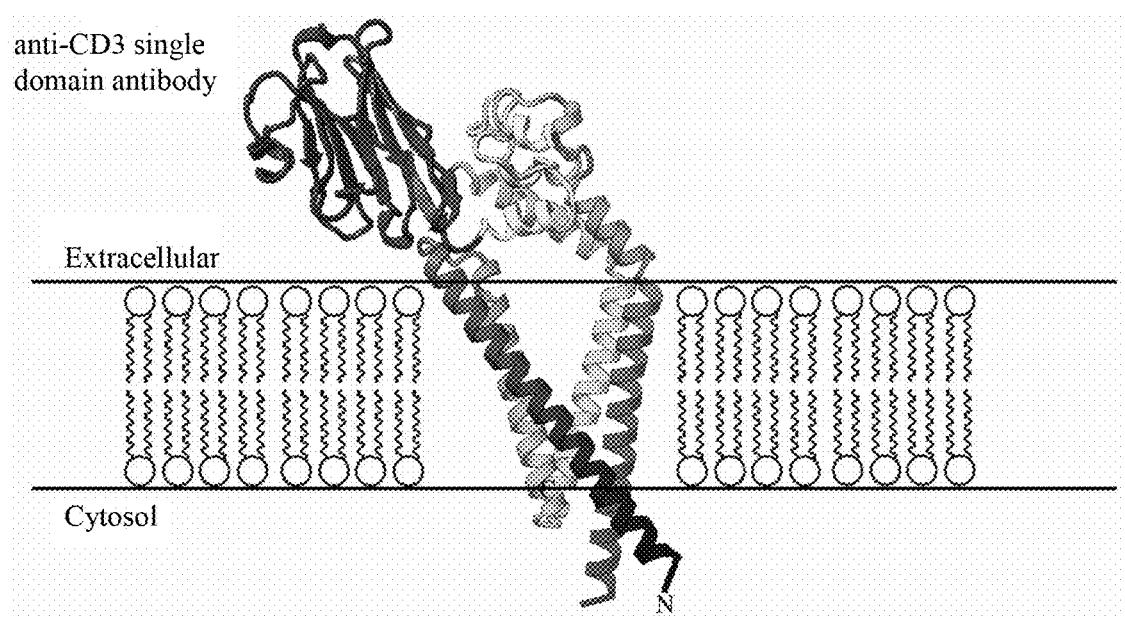
FIG. 1 is a schematic structural diagram of the fusion protein of the present invention.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of +20%, preferably within +10%, and most preferably within +5%.

Unless otherwise stated in the context, "a", "the" and similar terms used in the specification (especially in the following claims) should be understood as including singular and plural forms.

As used herein, the terms "CD3e" and "CD3 ε" can be used interchangeably.

As used herein, the terms "CD3e Nanobody™", "CD3e nb", "CD3e Nb", "CD3e Nanobody™", "anti-CD3 ε Nanobody™", and "anti-T cell Nanobody™" can be used interchangeably.

As used herein, the term "treating" or "treatment" refers to alleviating, reducing, ameliorating, relieving or controlling one or more clinical signs of a disease or disorder, and lowering, stopping, or reversing the progression of severity regarding the condition or symptom being treated.

According to the present invention, the pharmaceutical composition can be manufactured to a dosage form suitable for parenteral or oral administration, using techniques well known to those skilled in the art, including, but not limited to, injection (e.g., sterile aqueous solution or dispersion), sterile powder, tablet, troche, lozenge, pill, capsule, dispersible powder or granule, solution, suspension, emulsion, syrup, elixir, slurry, and the like.

The pharmaceutical composition according to the present invention may be administered by a parenteral route selected from the group consisting of: intraperitoneal injection, subcutaneous injection, intraepidermal injection, intradermal injection, intramuscular injection, intravenous injection, and intralesional injection. According to the present invention, the pharmaceutical composition may further comprise a pharmaceutically acceptable carrier which is widely used in pharmaceutically manufacturing techniques. For example, the pharmaceutically acceptable carrier can comprise one or more reagents selected from the group consisting of solvent, emulsifier, suspending agent, decomposer, binding agent, excipient, stabilizing agent, chelating agent, diluent, gelling agent, preservative, lubricant, absorption delaying agent, liposome, and the like. The selection and quantity of these reagents fall within the scope of the professional literacy and routine techniques of those skilled in the art.

According to the present invention, the pharmaceutically acceptable carrier comprises a solvent selected from the group consisting of water, normal saline, phosphate buffered saline (PBS), sugar-containing solution, aqueous solution containing alcohol, and combinations thereof.

As used herein, the term "nucleic acid". "nucleic acid sequence" or "nucleic acid fragment" refers to a sequence of deoxyribonucleotides or ribonucleotides in single- or double-stranded forms, and comprises known naturally occurring nucleotides or artificially chemical mimics. As used herein, the term "nucleic acid" is used interchangeably with the terms "gene", "cDNA". "mRNA", "oligonucleotide" and "polynucleotide".

Example 1

Preparation of Fusion Protein of Present Invention

In this example, the preparation process of the fusion protein comprising anti-CD3 single domain antibody and exosomal protein is as follows. The HEK-293T cell line (passages 4-25) and anti-CD3 single domain antibody-CD63 chimeric protein-expressing HEK-293T stable cell line will be loaded in COL2.5 NGCs with 500 mL of DMEM medium containing 50 mL of exosome-free FBS (Thermo Fisher Scientific). After culture for 3 days, the medium will be centrifuged at 2000 g for 15 min to remove cellular debris and then filtered with 0.2 μm filter paper. Then, the supernatant will be concentrated by ultrafiltration (Amicon® Ultra, 30 kDa, Merck Millipore) at 5000 g for 8 min. The collected supernatant will be processed with tangential flow filtration (MAP.03-plus TFF System, Lefo Science). Subsequently, the supernatants from parental HEK-293T cells will be filtered through membranes with 300 kDa cut-off and then resuspended in PBS; the supernatants from anti-CD3 single domain antibody-CD63 chimeric protein-expressing HEK-293T stable cells will be filtered through VHH-capturing membrane (GenScript) and then resuspended in PBS. All samples will be immediately use or stored at −80° C. for further use. For NTA analysis, these exosomes will be assayed by Zeta View® (Particle Metrix GmbH) to analyze the size distribution and concentration.

The anti-CD3 single domain antibody comprises an amino acid sequence of SEQ ID NO:1, SEQ ID NO:2, and SEQ ID NO:3, wherein the amino acid sequence of SEQ ID NO:1 is complementarity determining region 1 (CDR1), the amino acid sequence of SEQ ID NO:2 is CDR2, and the amino acid sequence of SEQ ID NO:3 is CDR3. The amino acid sequence of the fusion protein is SEQ ID NO:4.

The present invention also provides an isolated nucleic acid, encoding the amino acid sequence of the above mentioned fusion protein. The isolated nucleic acid consists of nucleotide sequence of SEQ ID NO:5.

The amino acid sequence of the anti-CD3 single domain antibody is SEQ ID NO: 6. The nucleotide sequence encoding the amino acid sequence of the anti-CD3 single domain antibody is SEQ ID NO:7. The amino acid sequence of the anti-CD3 single domain antibody is the heavy chain variable domain (VHH).

The schematic structural diagram of the fusion protein of the present invention is shown in FIG. 1, in which the anti-CD3 single domain antibody specifically binds to a CD3 ε.

Figure 2:
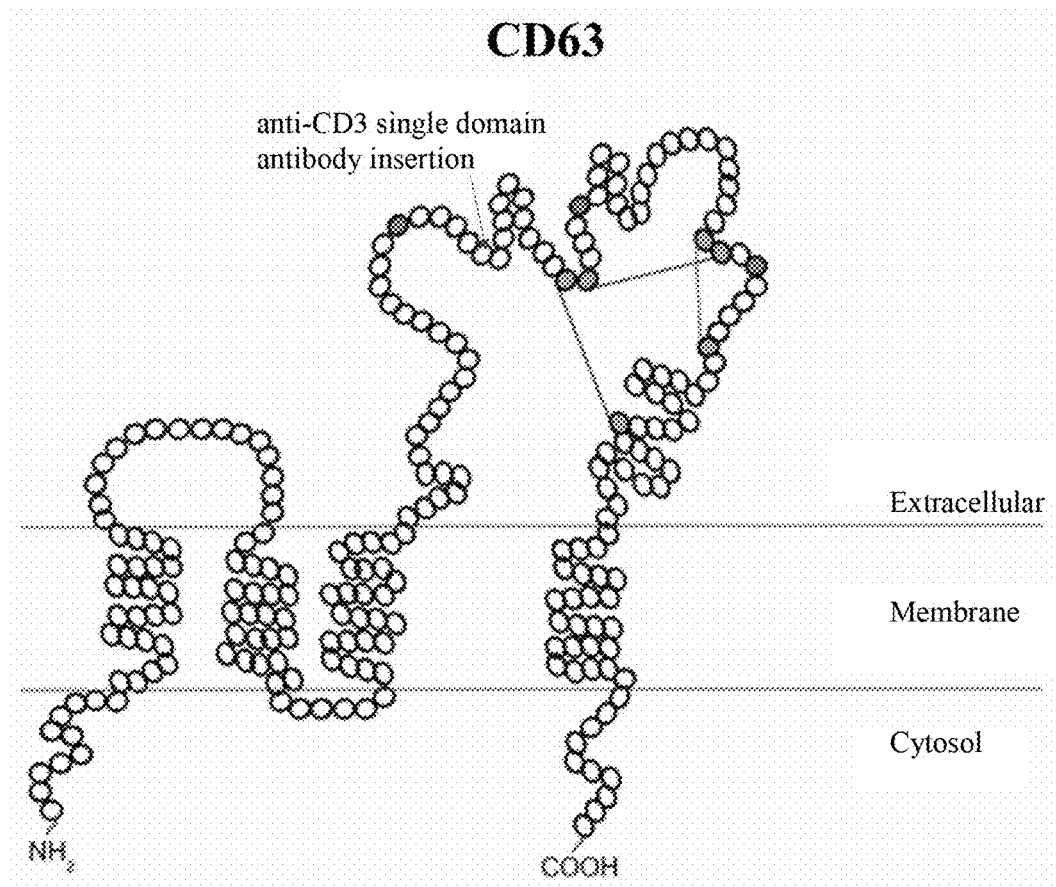
FIG. 2 shows the binding position of exosomal protein CD63 and anti-CD3 single domain antibody, in which the arrow indicates the inserting position of the anti-CD3 single domain antibody.

FIG. 2 shows the binding position of exosomal protein CD63 and anti-CD3 single domain antibody, in which the arrow indicates the inserting position of the anti-CD3 single domain antibody.

Example 2

Surface Plasmon Resonance (SPR) Analysis of Fusion Protein of Present Invention

In this example, the experimental procedure of the surface plasmon resonance (SPR) analysis of the fusion protein is as follows. The CM5 or NTA chip, research grade will be performed for SPR analysis by BIAcore T200 (Biacore-GE Healthcare, Piscataway, NJ). Briefly, dilute protein (CD3E recombinant protein) sample in the 10 mM buffer solutions (pH 4.0, 5.5 or 6.0) at the concentration range of 20 μg/mL to give maximum surface retention for immobilization on the chip, following the SURFACE PREPARATION process and choosing the condition of higher surface concentration of ligands (anti-CD3 single domain antibody: 25, 12.5, 6.25, 3.125, 1.5625 and 0.78125 nM) on the chip. Then the regeneration scouting and surface performance test, following REGENERATION SCOUTING and SURFACE PERFORMANCE TEST and then select REGENERATION METHOD to run the experiment. And then select BINDING ANALYSIS and DIRECT BINDING to investigate protein binding. The KINETIC ANALYSIS will be selected and choose MASS TRANSFER to run kinetic assay accompany with binding experiment. Data analysis and kinetic constants determine.

Figure 3:
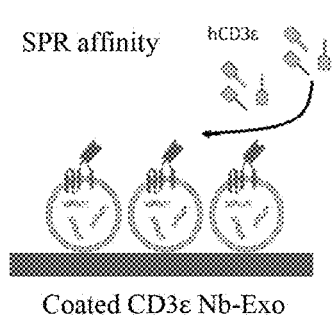
FIG. 3 shows the Exo surface plasmon resonance (SPR) analysis result of the fusion protein.
Figure 3:
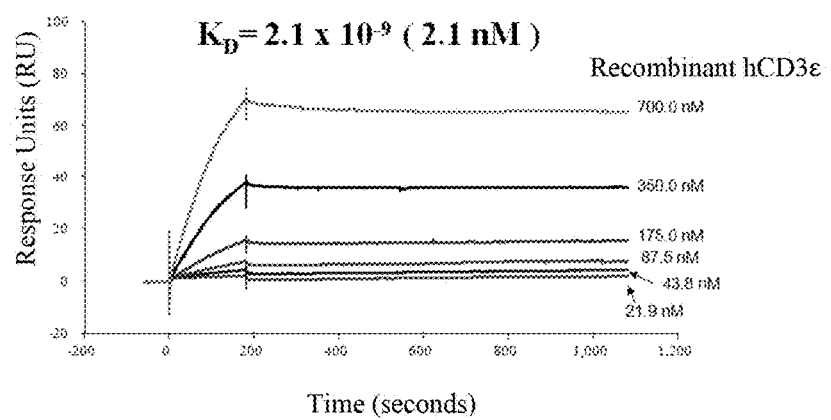

The Exo surface plasmon resonance (SPR) analysis result of the fusion protein is shown in FIG. 3. As shown in FIG. 3, the fusion protein ($1\times10^{11}$) was coated on CM5 chip, then its binding affinity was determined by using recombinant CD3E protein (700, 350, 175, 87.5, 43.8, 21.9 nM). The KD was determined as 2.1 nM.

Example 3

Evaluation of Effectiveness of Fusion Protein on Treating Cancer, Immunoregulation, and Activating Immune Cells The effectiveness of the fusion protein on treating cancer, immunoregulation, and activating immune cells is evaluated in this example.

Figure 4:
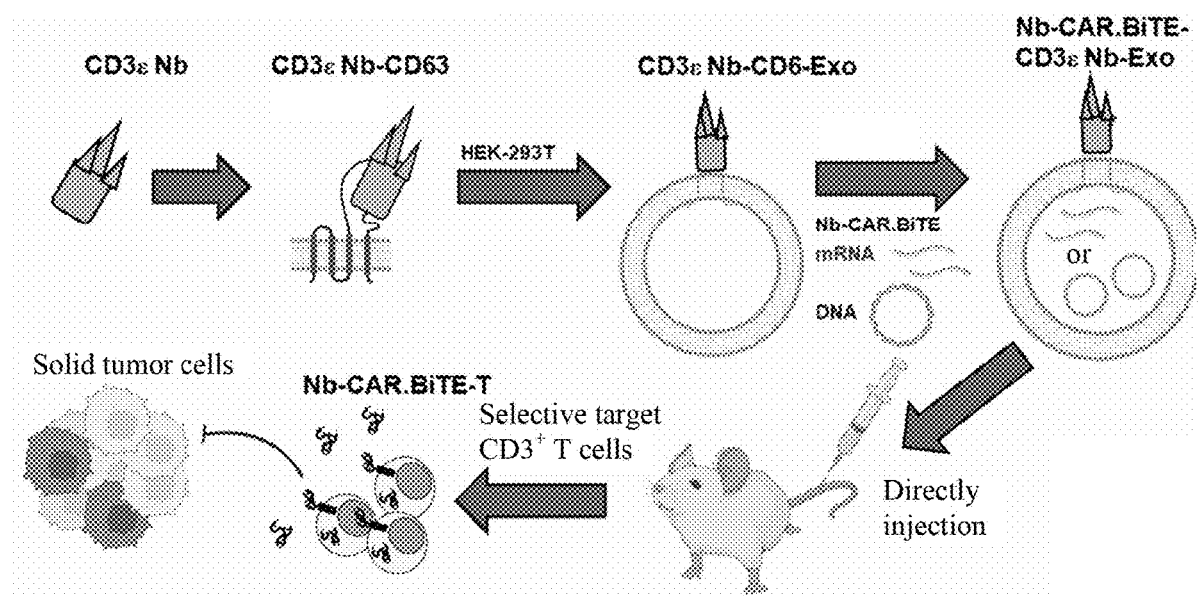
FIG. 4 is a schematic diagram of the effectiveness of the fusion protein on treating cancer, immunoregulation, and activating immune cells, in which CD3 ε Nb represents anti-CD3 single domain antibody, HEK-293T represents human embryonic kidney cell, Nb represents Nanobody™, CAR represents chimeric antigen receptor, BiTE represents bispecific T-cell engager, and Exo represents exosome.

FIG. 4 is a schematic diagram of the effectiveness of the fusion protein on treating cancer, immunoregulation, and activating immune cells, in which CD3 ε Nb represents anti-CD3 single domain antibody, HEK-293T represents human embryonic kidney cell, Nb represents Nanobody™, CAR represents chimeric antigen receptor, BiTE represents bispecific T-cell engager, and Exo represents exosome. As shown in FIG. 4, the sequence encodes anti-CD3 single domain antibody will be inserted into CD63 at the second ecto-loop for forming a CD63 chimeric protein with a cell surface-exposed anti-CD3 single domain antibody, then this construct will be transfected into HEK-293T to produce anti-CD3 single domain antibody-expressing Exo. The harvested exosomes will then be purified by using VHH-capsule column and then loading with DNA or mRNA encodes Nb-CAR.BiTE. This Nb-CAR.BiTE-CD3ε Nb-Exo will be directly injected into mice model that we hypothesized these exosomes will selectively reprogram $CD3^+$ T cells to express Nb-CAR and secret Nb-BiTE to active against solid tumor cells in vivo.

Figure 5:
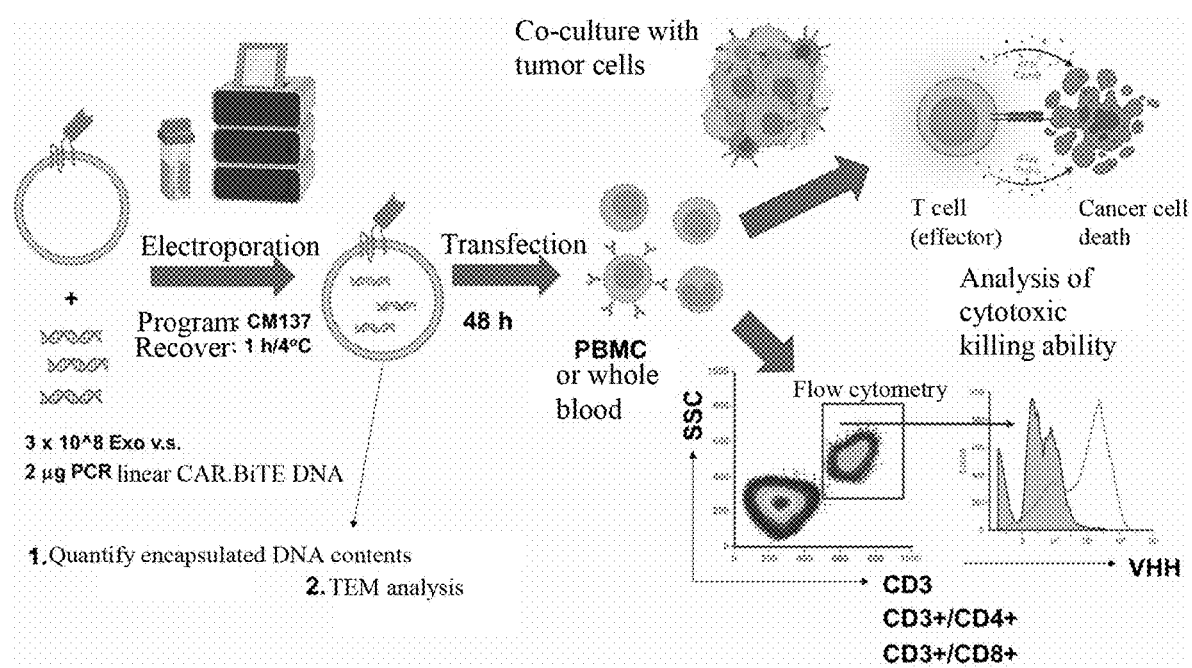
FIG. 5 is another schematic diagram of the effectiveness of the fusion protein on treating cancer, immunoregulation, and activating immune cells, in which PCR represents polymerase chain reaction, CAR represents chimeric antigen receptor, BiTE represents bispecific T-cell engager, Exo represents exosome, PBMC represents peripheral blood mononuclear cell, and TEM represents transmission electron microscope.

FIG. 5 is another schematic diagram of the effectiveness of the fusion protein on treating cancer, immunoregulation, and activating immune cells, in which PCR represents polymerase chain reaction, CAR represents chimeric antigen receptor, BiTE represents bispecific T-cell engager, Exo represents exosome, PBMC represents peripheral blood mononuclear cell, TEM represents transmission electron microscope, IFN γ represents interferon γ, TNF α represents tumor necrosis factor α, PFN represents perforin, GzmB represents Granzyme B, a serine protease that mediates the apoptotic signaling pathway of cytotoxic T lymphocytes and natural killer cells, SSC represents side scatter, and VHH represents heavy chain variable domain. As shown in FIG. 5, after electroporation of Exo and CAR.BiTE DNA at a ratio of ($3 \times 10^8$ Exo vs. 2 μg DNA) using LONZA 4D-Nucleofector electrotransfection program code CM137, and after one hour of recovery at 4° C., morphological observation with electron microscopy was performed, or transfected into human PBMC or whole blood for 48 hours, followed by co-culture with tumor cells. Changes in the ability to kill tumor cells using the LIVE/DEAD Cell-Mediated Cytotoxicity Assay were confirmed; or fluorescent antibodies were used to calibrate and analyze the expression of CD3, CD4, CD8, VHH, etc. on the cells using flow cytometry. The above experiments can confirm the transfection effect of fusion protein-coated CAR.BiTE DNA.

For transmission electron microscopy (TEM) analysis, the HEK-293T-derived exosomes will be fixed with 1% glutaraldehyde at 4° C. overnight after isolation. After washing, the exosomes will be loaded onto formvar carbon-coated grids, negatively stained with aqueous phosphotungstic acid for 1 min. The ultrastructure of these exosomes will be analyzed by TEM (JEOL JEM-1400, Tokyo, Japan).

Figure 6:
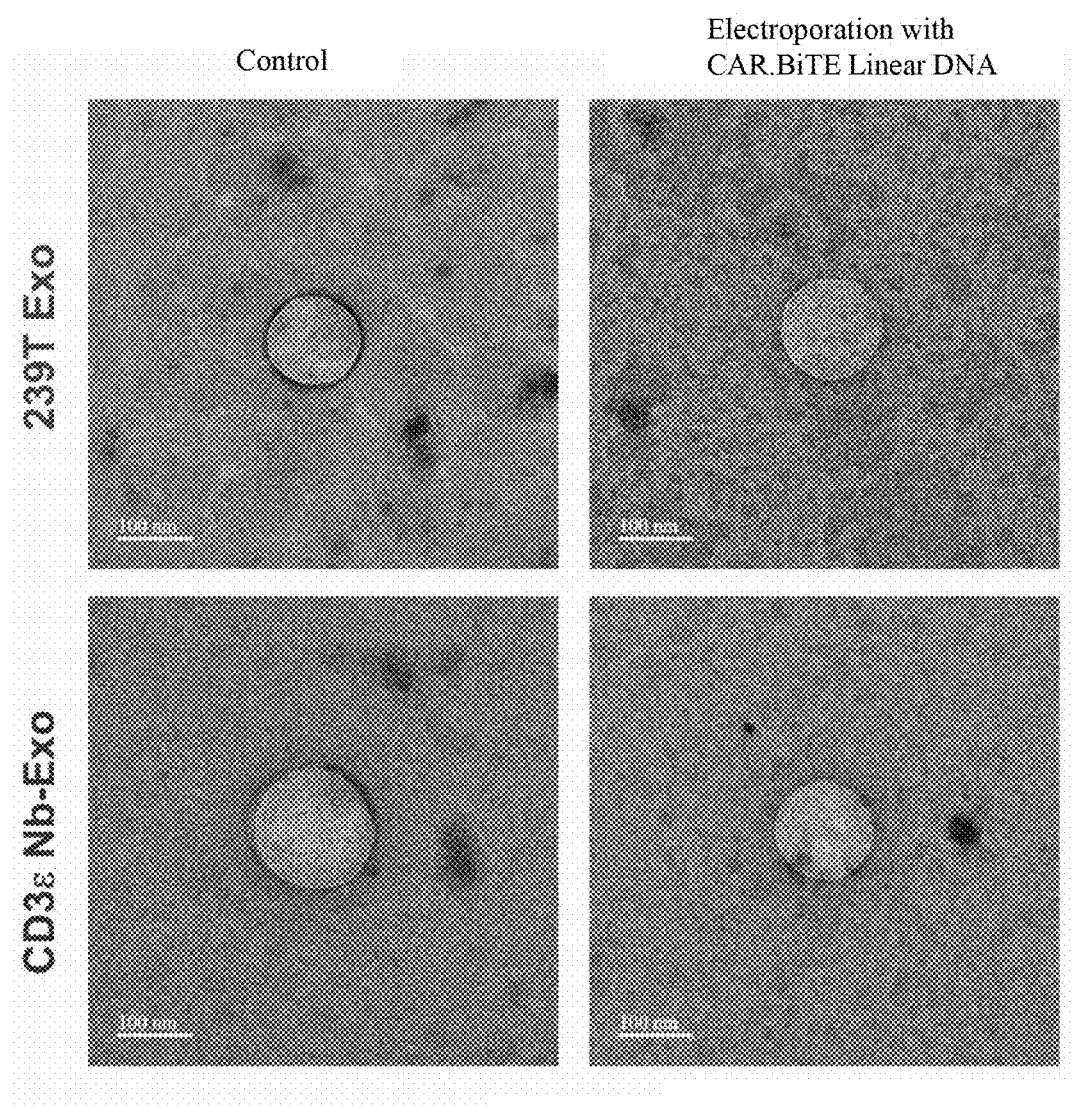
FIG. 6 shows the transmission electron microscope (TEM) result of the fusion protein, in which CD3 ε Nb represents anti-CD3 single domain antibody, Exo represents exosome, CAR represents chimeric antigen receptor, and BiTE represents bispecific T-cell engager.

FIG. 6 shows the transmission electron microscope (TEM) result of the fusion protein, in which CD3 ε Nb represents anti-CD3 single domain antibody, Exo represents exosome, CAR represents chimeric antigen receptor, and BiTE represents bispecific T-cell engager. As shown in FIG. 6, CAR.BiTE DNA@CD3ε Nb-Exo maintained exosomal ultrastructure and morphology. The unmodified and CD3ε Nb-engineered Exo with or without electroporation with CAR.BiTE-expressing DNA were assessed by TEM at 100,000×.

HEK293-derived Exo capable to encapsulate CAR-expressing DNA through electroporation. Unmodified and the fusion protein were electroporated with CAR.BiTE-expressing vector as the ratio as $3 \times 10^8$ Exo: 2 μg DNA by electroporation using LONZA 4D-Nucleofector. Then the Exo were incubated with DNase (1000 IU) for 30 min, and the incorporated CAR.BiTE DNA was quantified by qPCR using specific primers or by spectrophotometer at O.D. 260 and 280 nm.

Figure 7:
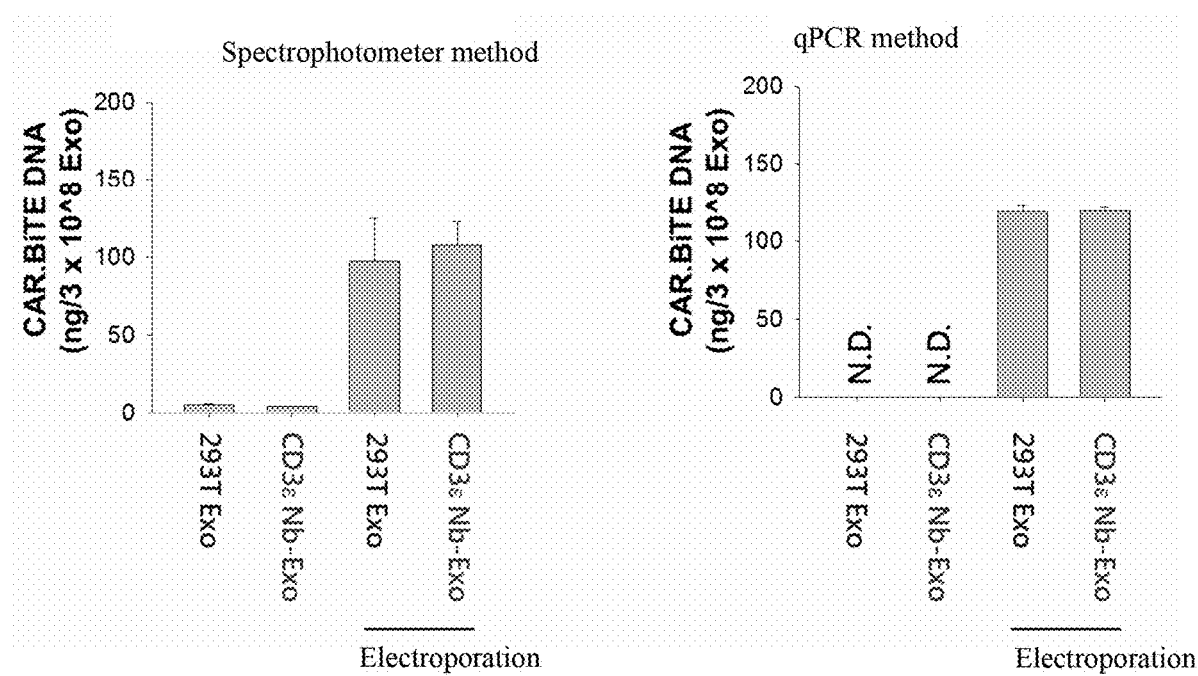
FIG. 7 shows the encapsulation efficiency of linear Nb-CAR.BiTE DNA into Exo through electroporation, in which Nb represents Nanobody™, CAR represents chimeric antigen receptor, BiTE represents bispecific T-cell engager, Exo represents exosome, CD3 ε Nb represents anti-CD3 single domain antibody, and qPCR represents quantitative polymerase chain reaction.

FIG. 7 shows the encapsulation efficiency of linear Nb-CAR.BiTE DNA into Exo through electroporation, in which Nb represents Nanobody™, CAR represents chimeric antigen receptor, BiTE represents bispecific T-cell engager, Exo represents exosome, CD3 ε Nb represents anti-CD3 single domain antibody, and qPCR represents quantitative polymerase chain reaction. As shown in FIG. 7, from the spectrophotometer and qPCR results, it is known that the electrotransfection method can coat approximately 100 ng CAR.BiTE DNA per $3 \times 10^8$ Exo.

Unmodified or fusion protein were electroporated with or without CAR.BiTE-expressing vector at the ratio as $3 \times 10^8$ Exo: 2 μg DNA, after purification, these Exo was added into $5 \times 10^5$ PBMC for 48 h, after 45 min of staining on ice, the expression level of Nb-CAR on $CD3^+$, $CD3^-$, $CD3^+/CD4^+$, $CD3^+/CD8^+$, $CD56^+$, $TCRγδ^+$, $CD14^+$, $CD19^+$ and $CD66b^+$ cells were measured by flow cytometry using specific antibodies.

Figure 8:
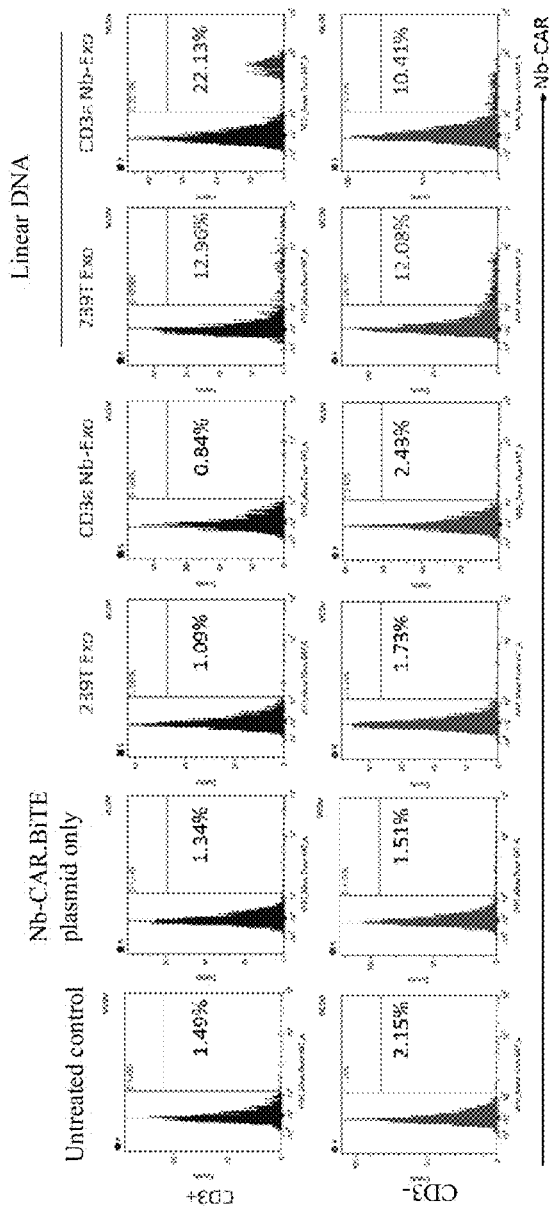
FIG. 8 shows testing for transfection efficiency of Nb-CAR.BiTE DNA-encapsulated electroporated Exo into peripheral blood mononuclear cells (PBMCs), in which Nb represents Nanobody™, CAR represents chimeric antigen receptor, BiTE represents bispecific T-cell engager, Exo represents exosome, CD3 ε Nb represents anti-CD3 single domain antibody, and WLSM represents weighted least square method.

FIG. 8 shows testing for transfection efficiency of Nb-CAR.BiTE DNA-encapsulated electroporated Exo into peripheral blood mononuclear cells (PBMCs), in which Nb represents Nanobody™, CAR represents chimeric antigen receptor, BiTE represents bispecific T-cell engager, Exo represents exosome, CD3 ε Nb represents anti-CD3 single domain antibody, and WLSM represents weighted least square method. As shown in FIG. 8, by comparing with unmodified Exo (293T Exo), CAR.BiTE DNA@CD3e Nb-Exo showed more efficiently transfection rate on CD3+ cells in contrast to CD3 cells. This result supported that the fusion protein exerts selective delivery transgene into $CD3^+$ cells.

Unmodified or fusion protein were electroporated with or without CAR.BiTE-expressing vector at the ratio as $3 \times 10^8$ Exo: 2 μg DNA, after purification, these Exo was added into $5 \times 10^5$ PBMC for 48 h, after 45 min of staining on ice, the expression level of Nb-CAR on $CD3^+$, $CD3^-$, $CD3^+/CD4^+$, $CD3^+/CD8^+$, cells were measured by flow cytometry using specific antibodies.

Figure 9:
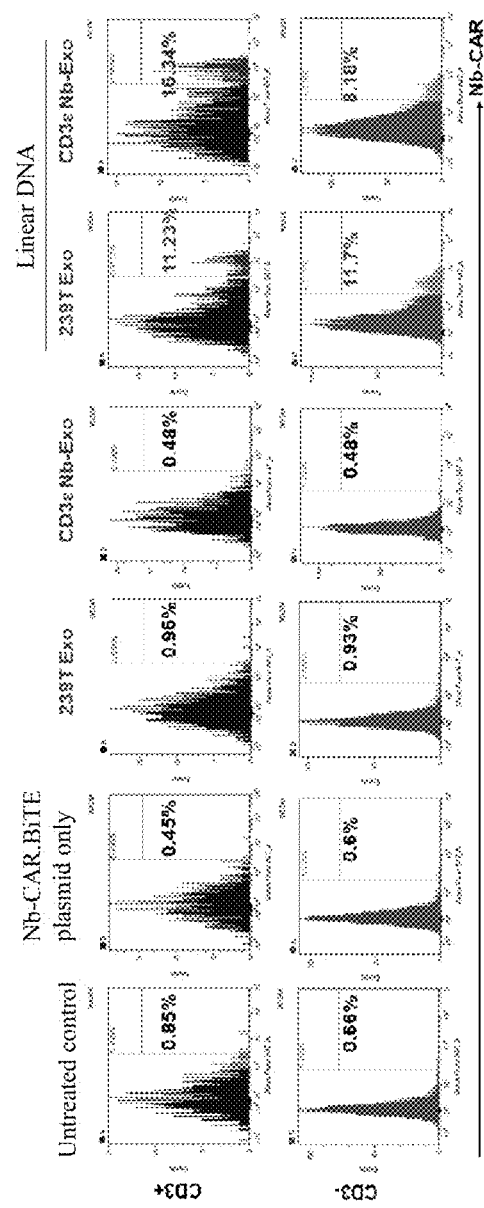
FIG. 9 shows testing for transfection efficiency of Nb-CAR.BiTE DNA-encapsulated electroporated Exo into peripheral blood mononuclear cells (PBMCs), in which Nb represents Nanobody™, CAR represents chimeric antigen receptor, BiTE represents bispecific T-cell engager, Exo represents exosome, and CD3 ε Nb represents anti-CD3 single domain antibody.

FIG. 9 shows testing for transfection efficiency of Nb-CAR.BiTE DNA-encapsulated electroporated Exo into peripheral blood mononuclear cells (PBMCs), in which Nb represents Nanobody™, CAR represents chimeric antigen receptor, BiTE represents bispecific T-cell engager, Exo represents exosome, and CD3 ε Nb represents anti-CD3 single domain antibody. As shown in FIG. 9, by comparing with unmodified Exo (293T Exo), CAR.BiTE DNA@CD3e Nb-Exo showed more efficiently transfection rate on $CD3^+/CD4^+$ and $CD3/CD8^+$ T cells. This result supported that the fusion protein exerts selective delivery transgene into $CD4^+$ and $CD8^+$ cells.

Unmodified or fusion protein were electroporated with or without CAR.BiTE-expressing vector at the ratio as $3 \times 10^8$ Exo: 2 μg DNA, after purification, these Exo was added into $5 \times 10^5$ PBMC for 48 h. after 45 min of staining on ice, the expression level of Nb-CAR on $CD3^+$, $CD3^-$, $CD3^+/CD4^+$, $CD3^+/CD8^+$, cells were measured by flow cytometry using specific antibodies.

Figure 10:
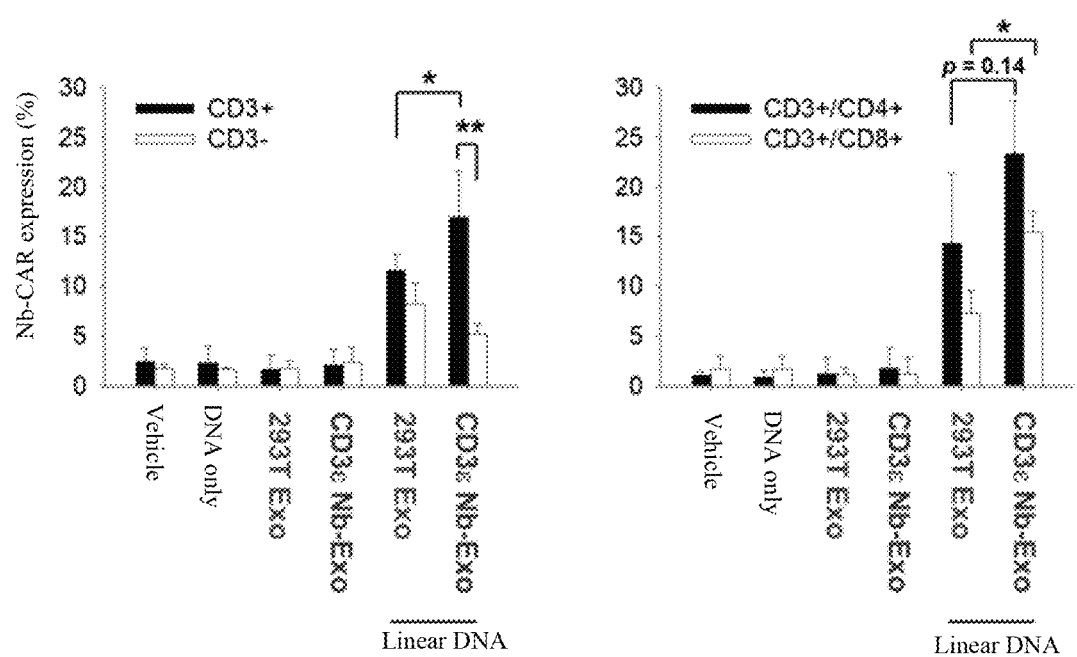
FIG. 10 shows testing for transfection efficiency of linear Nb-CAR.BiTE DNA-encapsulated electroporated Exo into PBMCs, in which Nb represents Nanobody™, CAR represents chimeric antigen receptor, Exo represents exosome, and CD3 ε Nb represents anti-CD3 single domain antibody.

FIG. 10 shows testing for transfection efficiency of linear Nb-CAR.BiTE DNA-encapsulated electroporated Exo into PBMCs, in which Nb represents Nanobody™, CAR represents chimeric antigen receptor, Exo represents exosome, and CD3 ε Nb represents anti-CD3 single domain antibody. As shown in FIG. 10. CAR.BiTE DNA@CD3e Nb-Exo showed more efficiently transfection rate on CD3$^+$, CD3$^+$/CD4$^+$ and CD3/CD8$^+$ T cells. This result supported that the fusion protein exerts selective delivery transgene into CD4$^+$ and CD8$^+$ cells.

Unmodified or fusion protein were electroporated with or without CAR.BiTE-expressing vector at the ratio as $3 \times 10^8$ Exo: 2 μg DNA, after purification, these Exo was added into 1 ml whole blood for 48 h, after 45 min of staining on ice, the expression level of Nb-CAR on CD3$^+$, CD3$^-$, CD3$^+$/CD4$^+$, CD3$^+$/CD8$^+$, cells were measured by flow cytometry using specific antibodies.

Figure 11:
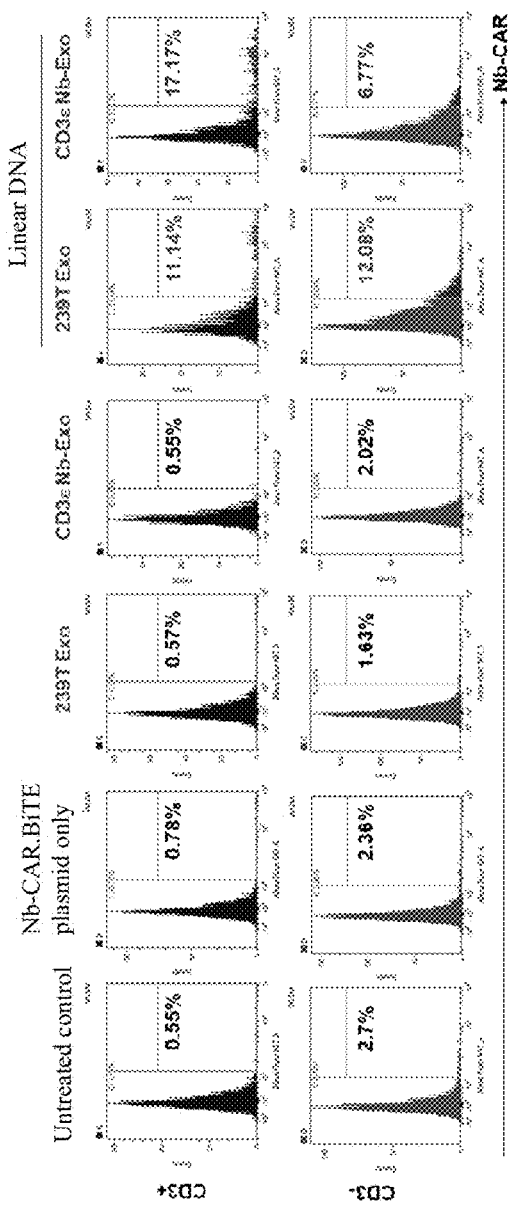
FIG. 11 shows testing for transfection efficiency of Nb-CAR.BiTE DNA-encapsulated electroporated Exo into whole blood, in which Nb represents Nanobody™, CAR represents chimeric antigen receptor, BiTE represents bispecific T-cell engager, Exo represents exosome, CD3 ε Nb represents anti-CD3 single domain antibody, and WLSM represents weighted least square method.

FIG. 11 shows testing for transfection efficiency of Nb-CAR.BiTE DNA-encapsulated electroporated Exo into whole blood, in which Nb represents Nanobody™, CAR represents chimeric antigen receptor, BiTE represents bispecific T-cell engager, Exo represents exosome, CD3 ε Nb represents anti-CD3 single domain antibody, and WLSM represents weighted least square method. As shown in FIG. 11, this result supported that the fusion protein exerts selective delivery transgene into CD3$^+$ cells of whole blood.

Unmodified or fusion protein were electroporated with or without CAR.BiTE-expressing vector at the ratio as $3 \times 10^8$ Exo: 2 μg DNA, after purification, these Exo was added into 1 ml whole blood for 48 h, after 45 min of staining on ice, the expression level of Nb-CAR on CD3$^+$, CD3$^-$, CD3$^+$/CD4$^+$, CD3$^+$/CD8$^+$, CD56$^+$, TCRγδ$^+$, CD14$^+$, CD19$^+$, and CD66b$^+$ cells were measured by flow cytometry using specific antibodies.

Figure 12:
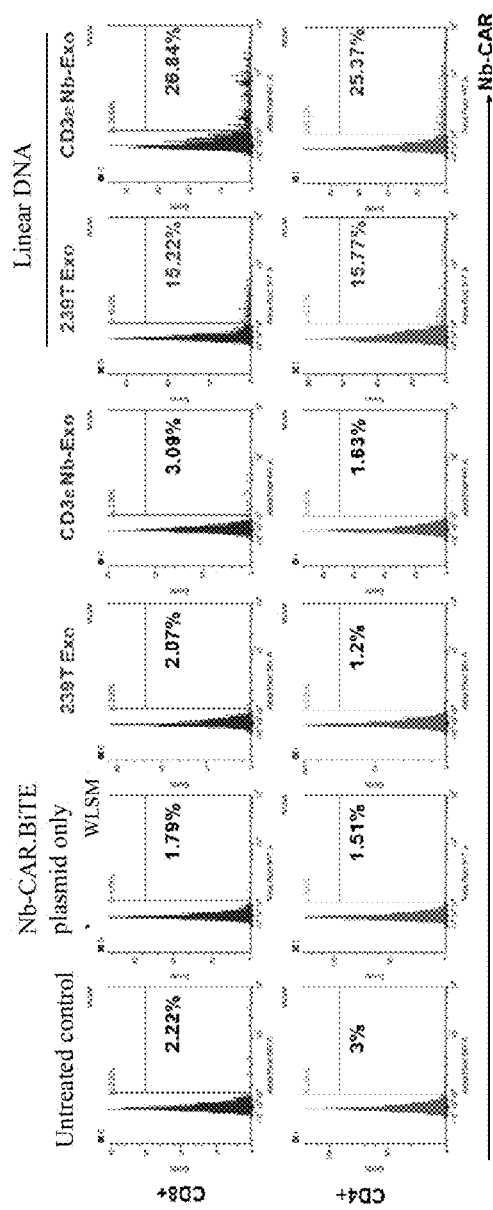
FIG. 12 shows testing for transfection efficiency of linear Nb-CAR.BiTE DNA-encapsulated electroporated Exo into whole blood, in which Nb represents Nanobody™, CAR represents chimeric antigen receptor, BiTE represents bispecific T-cell engager, Exo represents exosome, CD3 ε Nb represents anti-CD3 single domain antibody, and WLSM represents weighted least square method.

FIG. 12 shows testing for transfection efficiency of linear Nb-CAR.BiTE DNA-encapsulated electroporated Exo into whole blood, in which Nb represents Nanobody™, CAR represents chimeric antigen receptor, BiTE represents bispecific T-cell engager, Exo represents exosome, CD3 ε Nb represents anti-CD3 single domain antibody, and WLSM represents weighted least square method. As shown in FIG. 12, this result supported that the fusion protein exerts selective delivery transgene into CD3$^+$/CD4 and CD3$^+$/CD8$^+$ cells of whole blood.

Unmodified or fusion protein were electroporated with or without CAR.BiTE-expressing vector at the ratio as $3 \times 10^8$ Exo: 2 μg DNA, after purification, these Exo was added into 1 ml whole blood for 48 h, after 45 min of staining on ice, the expression level of Nb-CAR on CD3$^+$, CD3$^-$, CD3$^+$/CD4$^+$, and CD3$^+$/CD8$^+$ cells were measured by flow cytometry using specific antibodies.

Figure 13:
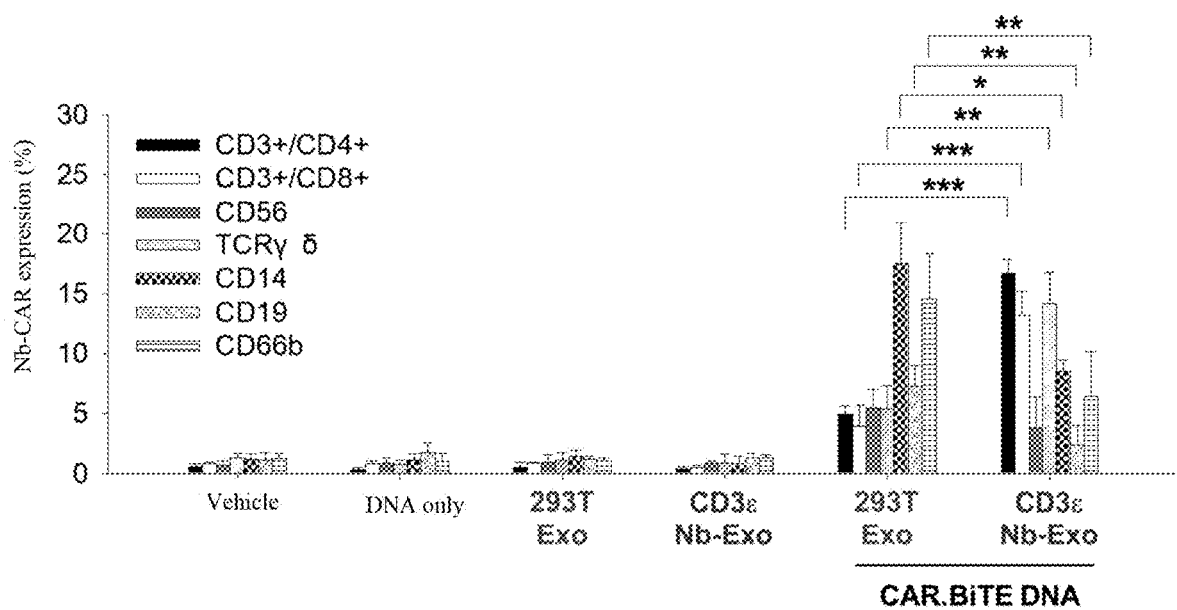
FIG. 13 shows testing for transfection efficiency of linear Nb-CAR.BiTE DNA-encapsulated electroporated Exo into whole blood, in which Nb represents Nanobody™, CAR represents chimeric antigen receptor, BiTE represents bispecific T-cell engager, Exo represents exosome, and CD3 ε Nb represents anti-CD3 single domain antibody.

FIG. 13 shows testing for transfection efficiency of linear Nb-CAR.BiTE DNA-encapsulated electroporated Exo into whole blood, in which Nb represents Nanobody™, CAR represents chimeric antigen receptor, BiTE represents bispecific T-cell engager, Exo represents exosome, and CD3 ε Nb represents anti-CD3 single domain antibody. As shown in FIG. 13, this result supported that the fusion protein exerts selective delivery transgene into CD3$^+$, CD3$^+$/CD4 and CD3$^+$/CD8$^+$ cells of whole blood.

Unmodified or fusion protein were electroporated with or without CAR.BiTE-expressing vector at the ratio as $3 \times 10^8$ Exo: 2 μg DNA, after purification, these Exo was added into 1 ml whole blood for 48 h, after 45 min of staining on ice, the expression level of Nb-CAR on CD3$^+$, CD3$^-$, CD3$^+$/CD4$^+$, CD3$^+$/CD8$^+$, cells were measured by flow cytometry using specific antibodies.

Figure 14:
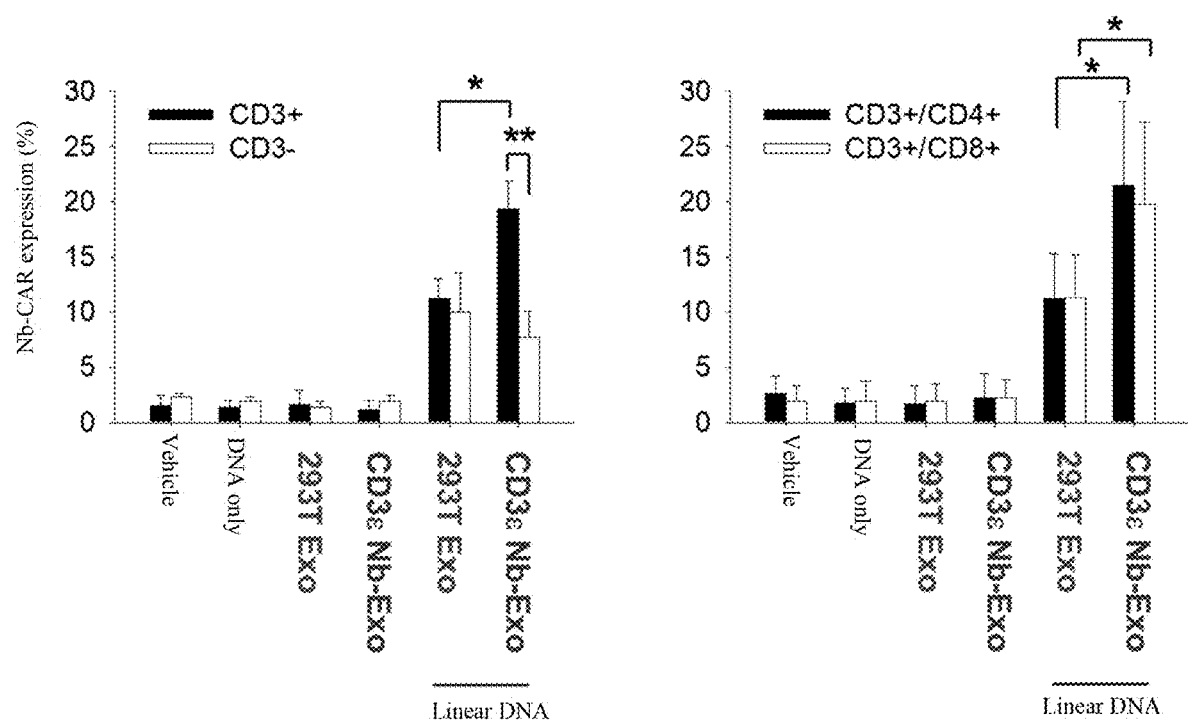
FIG. 14 shows testing for transfection efficiency of linear Nb-CAR.BiTE DNA-encapsulated electroporated Exo into whole blood, in which Nb represents Nanobody™, CAR represents chimeric antigen receptor, BiTE represents bispecific T-cell engager, Exo represents exosome, and CD3 ε Nb represents anti-CD3 single domain antibody.

FIG. 14 shows testing for transfection efficiency of linear Nb-CAR.BiTE DNA-encapsulated electroporated Exo into whole blood, in which Nb represents Nanobody™, CAR represents chimeric antigen receptor, BiTE represents bispecific T-cell engager, Exo represents exosome, and CD3 ε Nb represents anti-CD3 single domain antibody. As shown in FIG. 14, this result supported that the fusion protein exerts selective delivery transgene into CD3$^+$, CD3$^+$/CD4 and CD3$^+$/CD8$^+$ cells of whole blood.

Cytotoxic killing assay: CAR.BiTE-CD3ε Nb-Exo or unmodified exosomes-treated CD3$^+$ cells will be used as effector cells. Target cells (tumor cell lines) will be cocultured with the effector cells at the indicated ratios of effector/target (E:T) from 1:1 to 50:1 for 24 to 72 hours at 37° C. For the Live/Dead Cell Viability Assay, all the tumor cells will be stained with green-fluorescent calcein-AM before coculture, and then staining with red-fluorescent ethidium homodimer-1 after coculture will be used to label the dead cells, the dead tumor cells will be determined as green-fluorescent$^+$/red-fluorescent$^+$ cells according to the manufacturer's instructions (Thermo Fisher Scientific). The cell killing rates are presented as the percentages of the total cell population.

Figure 15:
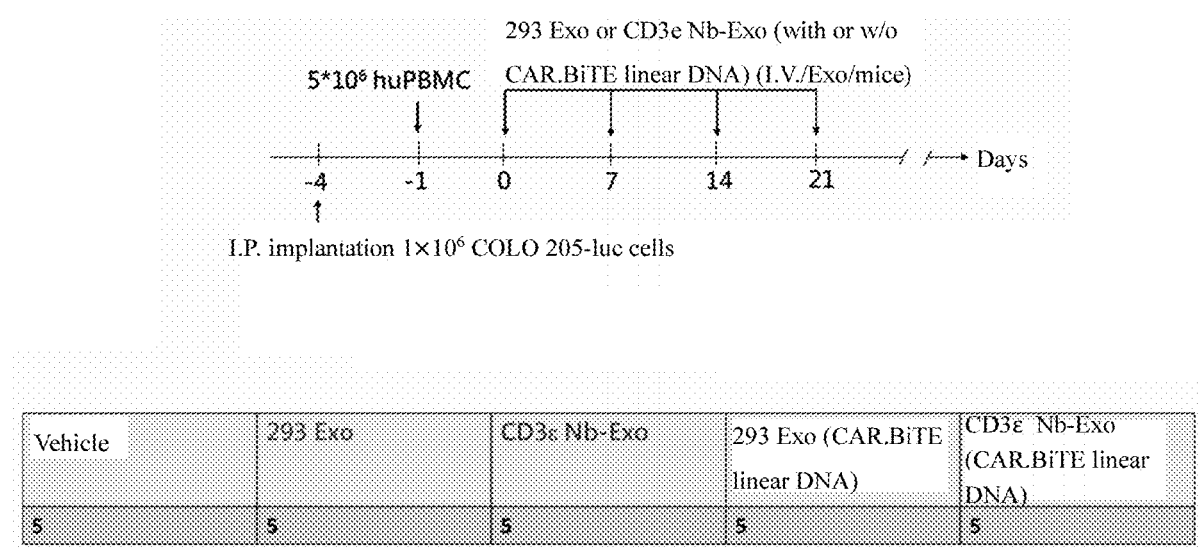
FIG. 15 shows the schematic representation of fusion protein in vivo chimeric antigen receptor T-cell therapy (CAR-T), in which PBMC-huNSG mice model was used, huPBMC represents human peripheral blood mononuclear cell, I.P. represents intraperitoneal, I.V. represents intravenous, CAR represents chimeric antigen receptor, BiTE represents bispecific T-cell engager, Exo represents exosome, CD3 ε Nb represents anti-CD3 single domain antibody, luc represents luciferase, the fourth dose has been administered, and blood has been collected to test the transfection efficiency. The number "5" means five mice per group.

Schematics representation of protocol for in vivo anti-tumor efficacy study of CAR.BiTE DNA@CD3ε Nb-Exo (FIG. 15). After 7 days of intraperitoneal implantation of COLO 205-luc cells ($1 \times 10^6$ cells), the mice (n=5) were tail vein injected with huPBMC ($5 \times 10^6$). On the next day, the mice were treated with or without unmodified or CD3ε Nb-Exo loaded with or without CAR.BiTE DNA ($3 \times 10^{10}$/mice) once a week for four weeks. The tumor growth was monitored by IVIS system through detecting the bioluminescent signals. After 7 days of the last injection, the mice were sacrificed, the splenocytes were harvested and the expression levels of Nb-CAR on each type of immune cells were determined by flow cytometry using specific antibodies against VHH, CD3, CD56, TCRγδ, CD14, CD19 and CD66b.

FIG. 15 shows the schematic representation of fusion protein in vivo chimeric antigen receptor T-cell therapy (CAR-T), in which PBMC-huNSG mice model was used, huPBMC represents human peripheral blood mononuclear cell, I.P. represents intraperitoneal, I.V. represents intravenous, CAR represents chimeric antigen receptor, BiTE represents bispecific T-cell engager, Exo represents exosome, CD3 ε Nb represents anti-CD3 single domain antibody, luc represents luciferase, the fourth dose has been administered, and blood has been collected to test the transfection efficiency. The number "5" means five mice per group.

Figure 16:
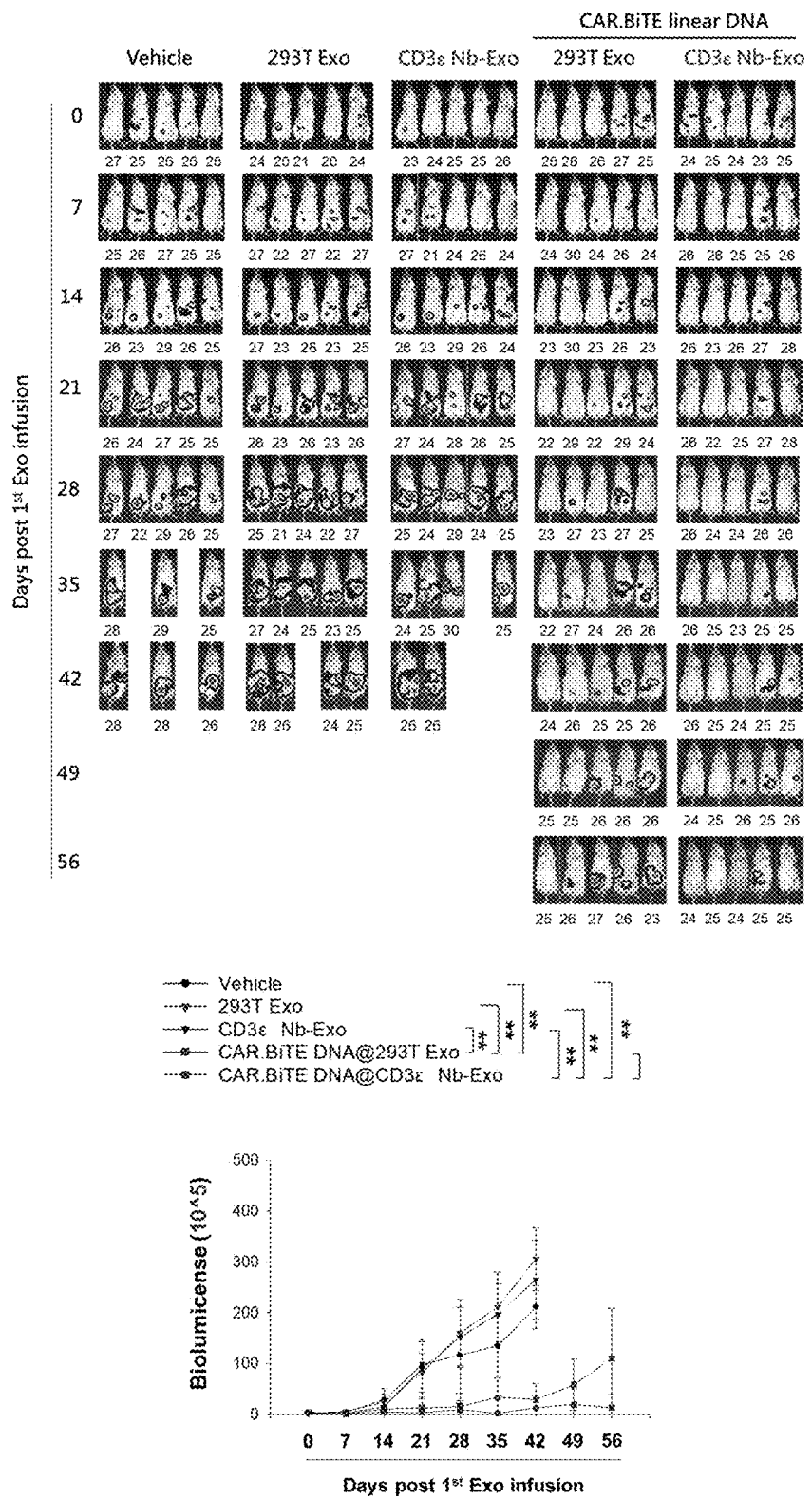
FIG. 16 shows the results of the effectiveness of the fusion protein on treating cancer, immunoregulation, and activating immune cells, in which CAR represents chimeric antigen receptor, BiTE represents bispecific T-cell engager, Exo represents exosome, and CD3 ε Nb represents anti-CD3 single domain antibody.

FIG. 16 shows the results of the effectiveness of the fusion protein on treating cancer, immunoregulation, and activating immune cells, in which CAR represents chimeric antigen receptor, BiTE represents bispecific T-cell engager, Exo represents exosome, and CD3 ε Nb represents anti-CD3 single domain antibody. As shown in FIG. 16, CAR.BiTE DNA@CD3e Nb-Exo elicited superior anti-tumor activity by comparing with other mice groups.

Figure 17:
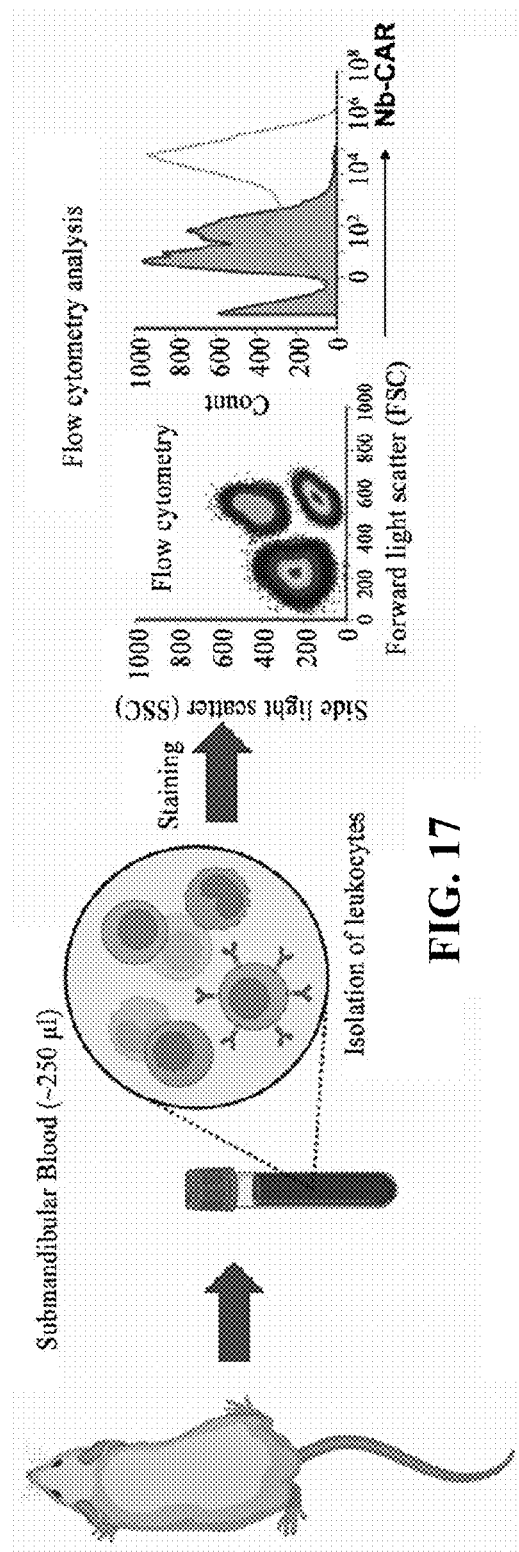
FIG. 17 shows the results of the effectiveness of the fusion protein on treating cancer, immunoregulation, and activating immune cells, in which Nb represents Nanobody™, and CAR represents chimeric antigen r.

Schematics representation of protocol for in vivo anti-tumor efficacy study of CAR.BiTE DNA@CD3ε Nb-Exo (FIG. 17). After 7 days of intraperitoneal implantation of COLO 205-luc cells ($1 \times 10^6$ cells), the mice (n=5) were tail vein injected with huPBMC ($5 \times 10^6$). On the next day, the mice were treated with or without unmodified or CD3ε Nb-Exo loaded with or without CAR.BiTE DNA ($3 \times 10^{10}$/mice) once a week for four weeks. After 7 days of the last injection, the mice were sacrificed, the submandibular blood were harvested and the expression levels of Nb-CAR on each type of immune cells were determined by flow cytometry using specific antibodies against VHH and CD3.

FIG. 17 shows the results of the effectiveness of the fusion protein on treating cancer, immunoregulation, and activating immune cells, in which Nb represents Nanobody™, and CAR represents chimeric antigen receptor. This result supported that the fusion protein exerts selective delivery transgene into CD3+, CD3+/CD4 and CD3+/CD8+ cells of blood cells from PBMC-humanized NSG mice.

Figure 18:
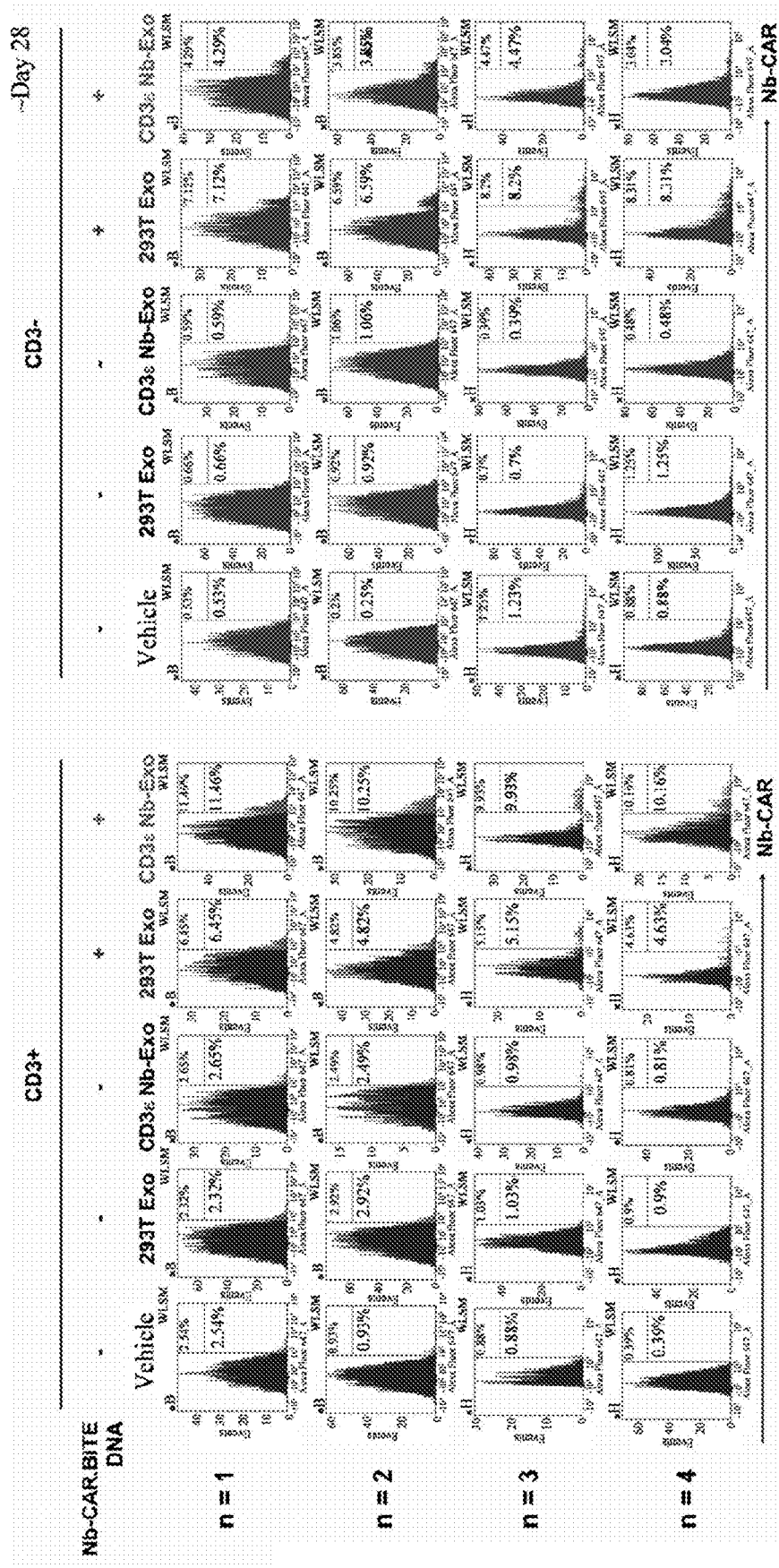
FIG. 18 shows the results of the effectiveness of the fusion protein on treating cancer, immunoregulation, and activating immune cells, the results of FIG. 18 showing data from the experimental design shown in FIG. 17, in which Nb represents Nanobody™, and CAR represents chimeric antigen receptor, Exo represents exosome, CD3 ε Nb represents anti-CD3 single domain antibody, and BiTE represents bispecific T-cell engager.

FIG. 18 shows the results of the effectiveness of the fusion protein on treating cancer, immunoregulation, and activating immune cells, the results of FIG. 18 showing data from the experimental design shown in FIG. 17, in which Nb represents Nanobody™, and CAR represents chimeric antigen receptor, Exo represents exosome, CD3 ε Nb represents anti-CD3 single domain antibody, and BiTE represents bispecific T-cell engager.

Figure 19:
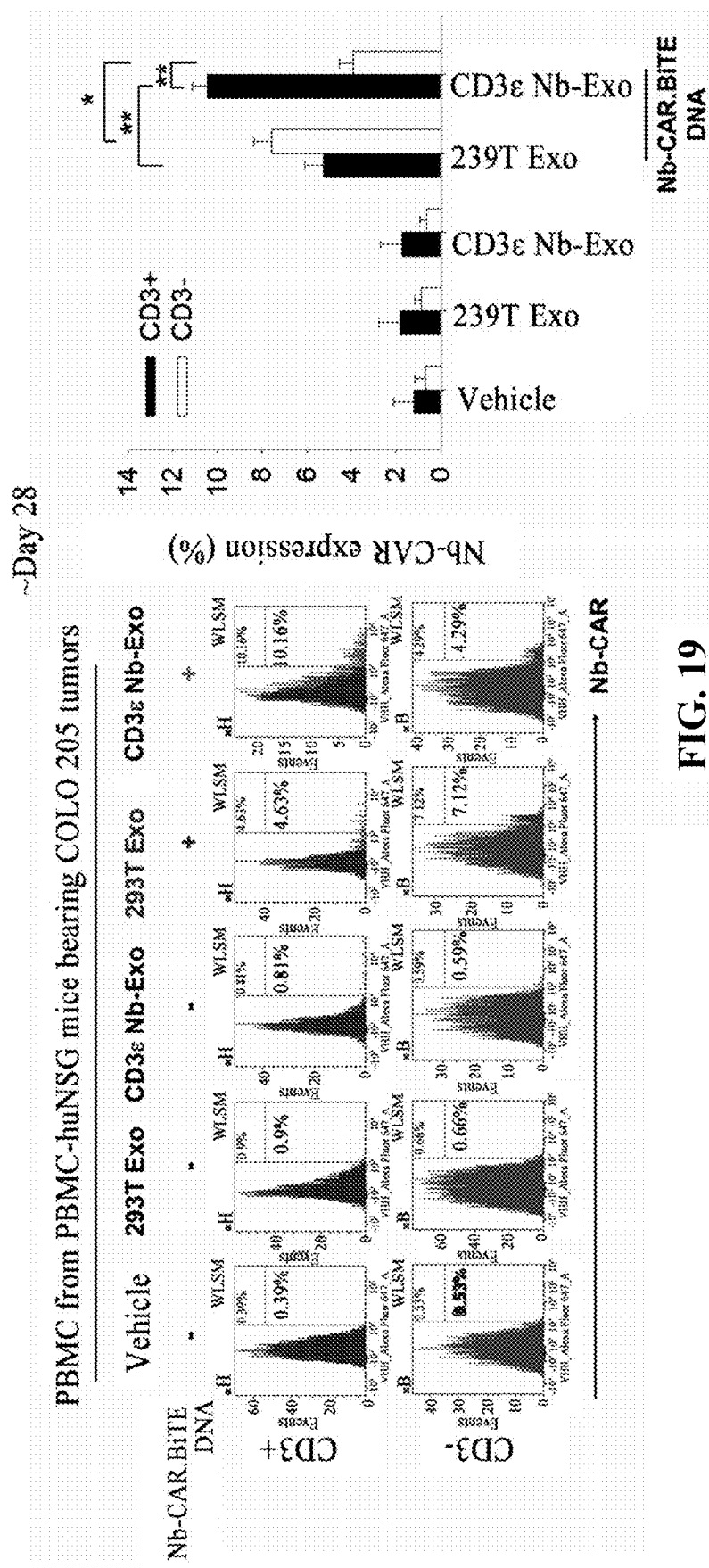
FIG. 19 shows the results of the effectiveness of the fusion protein on treating cancer, immunoregulation, and activating immune cells, and the flow plots in FIG. 19 are representative derived from the flow plots in FIG. 18, in which Nb represents Nanobody™, CAR represents chimeric antigen receptor, Exo represents exosome, CD3 ε Nb represents anti-CD3 single domain antibody, BiTE represents bispecific T-cell engager, and PBMC represents peripheral blood mononuclear cell.

FIG. 19 shows the results of the effectiveness of the fusion protein on treating cancer, immunoregulation, and activating immune cells, and the flow plots in FIG. 19 are representative derived from the flow plots in FIG. 18, in which Nb represents Nanobody™, CAR represents chimeric antigen receptor, Exo represents exosome, CD3 ε Nb represents anti-CD3 single domain antibody, BiTE represents bispecific T-cell engager, and PBMC represents peripheral blood mononuclear cell. As shown in FIGS. 18 and 19, this result supported that the fusion protein exerts selective delivery transgene into CD3+ cells of blood cells from PBMC-humanized NSG mice.

In summary, the fusion protein of the present invention has the effects on treating cancer, immunoregulation and activating immune cells by surface plasmon resonance (SPR), analysis of cytotoxic killing ability, animal experiment, electroporation experiment, testing for transfection efficiency, flow cytometry analysis, in vivo chimeric antigen receptor T-cell therapy (CAR-T), and penetrating the fusion protein into solid tumors and secreting bispecific T-cell engager (BiTE), and activating peripheral immune cells.

Although the present invention has been described with reference to the preferred embodiments, it will be apparent to those skilled in the art that a variety of modifications and changes in form and detail may be made without departing from the scope of the present invention defined by the appended claims.

---

What is claimed is:

1. A fusion protein, comprising an anti-CD3 single domain antibody and an exosomal protein, wherein the anti-CD3 single domain antibody comprises an amino acid sequence of SEQ ID NO:1, SEQ ID NO:2, and SEQ ID NO:3, and the amino acid sequence of the fusion protein is SEQ ID NO:4.

2. The fusion protein according to claim 1, wherein the anti-CD3 single domain antibody specifically binds to a CD3 ε.

3. The fusion protein according to claim 1, wherein the exosomal protein is CD63.

4. The fusion protein according to claim 1, wherein the amino acid sequence of SEQ ID NO: 1 is complementarity determining region 1 (CDR1), the amino acid sequence of SEQ ID NO: 2 is CDR2, and the amino acid sequence of SEQ ID NO:3 is CDR3.

5. The fusion protein according to claim 1, wherein the anti-CD3 single domain antibody is an anti-T cell single domain antibody.

6. An isolated nucleic acid, encoding an amino acid sequence of a fusion protein comprising an anti-CD3 single domain antibody and an exosomal protein, wherein the anti-CD3 single domain antibody comprises an amino acid sequence of SEQ ID NO:1, SEQ ID NO: 2, and SEQ ID NO:3, and the isolated nucleic acid consists of SEQ ID NO:5.

7. A pharmaceutical composition, comprising the fusion protein according to claim 1 and a pharmaceutically acceptable carrier.

8. The pharmaceutical composition according to claim 7, wherein the anti-CD3 single domain antibody specifically binds to a CD3 ε.

9. The pharmaceutical composition according to claim 7, wherein the exosomal protein is CD63.

10. The pharmaceutical composition according to claim 7, wherein the amino acid sequence of SEQ ID NO: 1 is complementarity determining region 1 (CDR1), the amino acid sequence of SEQ ID NO:2 is CDR2, and the amino acid sequence of SEQ ID NO:3 is CDR3.

11. The pharmaceutical composition according to claim 7, wherein the anti-CD3 single domain antibody is an anti-T cell single domain antibody.

* * * * *

SEQUENCE LISTING

```
Sequence total quantity: 7
SEQ ID NO: 1              moltype = AA   length = 8
FEATURE                   Location/Qualifiers
source                    1..8
                          mol_type = protein
                          organism = synthetic construct
SEQUENCE: 1
GVIFKNEY                                                                   8

SEQ ID NO: 2              moltype = AA   length = 8
FEATURE                   Location/Qualifiers
source                    1..8
                          mol_type = protein
                          organism = synthetic construct
SEQUENCE: 2
ASPGGTIT                                                                   8

SEQ ID NO: 3              moltype = AA   length = 23
FEATURE                   Location/Qualifiers
source                    1..23
                          mol_type = protein
                          organism = synthetic construct
SEQUENCE: 3
ALDPSTTSWS IIRHGPSLWR YSG                                                 23

SEQ ID NO: 4              moltype = AA   length = 370
FEATURE                   Location/Qualifiers
source                    1..370
                          mol_type = protein
                          organism = synthetic construct
SEQUENCE: 4
MAVEGGMKCV KFLLYVLLLA FCACAVGLIA VGVGAQLVLS QTIIQGATPG SLLPVVIIAV          60
GVFLFLVAFV GCCGACKENY CLMITFAIFL SLIMLVEVAA AIAGYVFRDK VMSEFNNNFR         120
QQMENYPKNN HTASAHVQLV ESGGGSVQAG GSLRLSCTVS GVIFKNEYMG WFRQAPGKER         180
EGVAAASPGG TITYYGDSVK GRFTISRDNA KNTVYLQMNR LKPEDTAMYY CALDPSTTSW         240
SIIRHGPSLW RYSGRGTQVT VSSGSSILDR MQADFKCCGA ANYTDWEKIP SMSKNRVPDS         300
CCINVTVGCG INFNEKAIHK EGCVEKIGGW LRKNVLVVAA AALGIAFVEV LGIVFACCLV         360
KSIRSGYEVM                                                               370

SEQ ID NO: 5              moltype = DNA   length = 1119
FEATURE                   Location/Qualifiers
source                    1..1119
                          mol_type = other DNA
                          organism = synthetic construct
SEQUENCE: 5
atggccgtgg agggcggcat gaagtgcgtg aagttcctgc tgtacgtgct gctgctggcc         60
ttctgcgcct gtgccgtagg ccttatcgcc gttggcgtgg gtgcgcagct ggtcctttct        120
cagaccataa tccaaggagc cacccccggc agcctgctgc ccgtggtgat catcgctgtg        180
ggggtcttcc tgttcctggt ggccttcgtg ggctgctgcg gcgcctgcaa ggagaactac        240
tgcctgatga tcaccttcgc catcttcctg agcctgatca tgctggtgga ggtggccgcc        300
gccatcgccg gctacgtgtt cagagacaag gtgatgagcg agttcaacaa caacttcaga        360
cagcagatgg agaactaccc caagaacaac cacaccgcca gcgctcatgt gcagctggtg        420
```

-continued

```
gagtctgggg gaggctcggt gcaggctggg gggtctctga gactctcctg tacagtgtct    480
ggagtcatct ttaagaacga gtacatgggc tggttccgcc aggcccccagg gaaggagcgc   540
gaggggtcg   cagcagcttc gcctggtgga acgattacat actatgggga ctccgtgaag   600
ggccgattca ccatctcccg agacaatgcc aagaacacgg tgtatctgca aatgaaccgc    660
ctgaaacctg aggacactgc catgtactac tgtgcgttgg atccctcgac tacgtcatgg    720
tctatcatcc gccacggtcc atcgctttgg cgttatagcg gccggggac   ccaggtcacc   780
gtctcctcag gatccagcat cctggacaga atgcaagccg acttcaagtg ctgcggcgcc    840
gccaactaca ccgactggga gaagatccct agcatgagca agaacagagt gcccgacagc    900
tgctgcatca acgtgaccgt gggctgcggc atcaacttca acgagaaggc catccacaag    960
gagggctgcg tggagaagat cggtggctgg ctgcgcaaga acgttctggt ggtggccgcc   1020
gccgccttag gcatcgcctt cgtggaggtg ctgggtatcg tgttcgcctg ctgcctggtg   1080
aagagcatca gatccggcta tgaggtaatg ggcgcgccg                          1119

SEQ ID NO: 6            moltype = AA  length = 128
FEATURE                 Location/Qualifiers
source                  1..128
                        mol_type = protein
                        organism = synthetic construct
SEQUENCE: 6
HVQLVESGGG SVQAGGSLRL SCTVSGVIFK NEYMGWFRQA PGKEREGVAA ASPGGTITYY    60
GDSVKGRFTI SRDNAKNTVY LQMNRLKPED TAMYYCALDP STTSWSIIRH GPSLWRYSGR   120
GTQVTVSS                                                            128

SEQ ID NO: 7            moltype = DNA  length = 384
FEATURE                 Location/Qualifiers
source                  1..384
                        mol_type = other DNA
                        organism = synthetic construct
SEQUENCE: 7
catgtgcagc tggtggagtc tgggggaggc tcggtgcagg ctggggggtc tctgagactc     60
tcctgtacag tgtctggagt catctttaag aacgagtaca tgggctggtt ccgccaggcc   120
ccagggaagg agcgcgaggg ggtcgcagca gcttcgcctg gtggaacgat tacatactat   180
ggggactccg tgaagggccg attcaccatc tcccgagaca atgccaagaa cacggtgtat   240
ctgcaaatga accgcctgaa acctgaggac actgccatgt actactgtgc gttggatccc   300
tcgactacgt catggtctat catccgccac ggtccatcgc tttggcgtta tagcggccgg   360
gggacccagg tcaccgtctc ctca                                          384
```